United States Patent
Bahn et al.

(10) Patent No.: US 9,459,266 B2
(45) Date of Patent: Oct. 4, 2016

(54) MARKER FOR RESPONSE TO ANTIDEPRESSANT THERAPY

(71) Applicant: Cambridge Enterprise Limited, Cambridge, Cambridgeshire (GB)

(72) Inventors: Sabine Bahn, Cambridge (GB); Man Kuan Chan, Cambridge (GB); Viktoria Stelzhammer, Cambridge (GB)

(73) Assignee: Cambridge Enterprise Limited, Cambridge, Cambridgeshire (GB)

( * ) Notice: Subject to any disclaimer, the term of this patent is extended or adjusted under 35 U.S.C. 154(b) by 0 days.

(21) Appl. No.: 14/890,584

(22) PCT Filed: May 13, 2014

(86) PCT No.: PCT/GB2014/051457
§ 371 (c)(1),
(2) Date: Nov. 11, 2015

(87) PCT Pub. No.: WO2014/184534
PCT Pub. Date: Nov. 20, 2014

(65) Prior Publication Data
US 2016/0116492 A1  Apr. 28, 2016

(30) Foreign Application Priority Data
May 13, 2013 (GB) ................................. 1308518.8

(51) Int. Cl.
*G01N 33/92* (2006.01)
*G01N 33/68* (2006.01)

(52) U.S. Cl.
CPC .......... *G01N 33/92* (2013.01); *G01N 33/6896* (2013.01); *G01N 2333/775* (2013.01); *G01N 2800/304* (2013.01); *G01N 2800/52* (2013.01)

(58) Field of Classification Search
None
See application file for complete search history.

(56) References Cited

FOREIGN PATENT DOCUMENTS

WO    WO 2014/184534 A1    11/2014

OTHER PUBLICATIONS

International Search Report from International Patent Application No. PCT/GB2014/051457, Mailed Jul. 24, 2014, application now published as International Publication No. WO2014/184534 on Nov. 20, 2014.

*Primary Examiner* — Heidi Reese
(74) *Attorney, Agent, or Firm* — McDermott Will & Emery LLP

(57) ABSTRACT

The invention relates to the use of ApoA4 as biomarker for predicting whether a patient will respond to antidepressant treatment. The invention further relates to methods and kits for predicting whether a patient will respond to antidepressant treatment using said biomarker.

20 Claims, 5 Drawing Sheets

MARKER FOR RESPONSE TO ANTIDEPRESSANT THERAPY

CROSS-REFERENCE TO RELATED APPLICATIONS

This application is a U.S. National Stage of International Patent Application No. PCT/GB2014/051457, filed May 13, 2014, which claims the benefit of priority of GB Application No. 1308518.8, filed May 13, 2013, each of which is incorporated herein by reference in its entirety.

FIELD OF THE INVENTION

The invention relates to a biomarker for predicting whether a patient will respond to antidepressant treatment. The invention further relates to methods and kits for predicting whether a patient will respond to antidepressant treatment using said biomarker.

BACKGROUND OF THE INVENTION

Major depressive disorder is a mental disorder characterized by a pervasive low mood, low self-esteem, and loss of interest or pleasure in normally enjoyable activities. The term "major depressive disorder" (which is also known as clinical depression, major depression, unipolar depression, or unipolar disorder) was selected by the American Psychiatric Association for this symptom cluster under mood disorders in the 1980 version of the *Diagnostic and Statistical Manual of Mental Disorders* (DSM-IV) classification, and has become widely used since.

The general term depression is often used to describe the disorder, but as it is also used to describe a depressed mood, more precise terminology is preferred in clinical and research use. Major depression is a disabling condition which adversely affects a person's family, work or school life, sleeping and eating habits, and general health. In the United States, approximately 3.4% of people with major depression commit suicide, and up to 60% of all people who commit suicide have depression or another mood disorder.

Major depressive disorder (MDD) is the most prevalent disabling and costly psychiatric disorder, with a lifetime prevalence of 16-20%. Current diagnoses are based on clinical decisions guided by subjective interview-based assessments. Treatment typically involves use of antidepressant medications which is traditionally based on a 'hit and miss' approach. To date, over 20 antidepressant medications have been approved for clinical application by the Food and Drug Administration. However, despite this wide selection of medications, there are a number of pressing problems associated with this treatment approach.

The success rate of treatment is only approximately 50%. The large proportion of non-responding patients requires additional extended and costly treatment as well as switching of antidepressants to treat symptoms that can last several months. The side effects associated with the prescription of higher therapeutic doses of antidepressants along with the prolonged treatment duration usually results in treatment non-adherence and disease relapse. Relapse increases the risk to further recurrences substantially. There are currently no means to predict which patients will benefit the most from the selection of available antidepressants. Common approaches to increase therapeutic efficacy rely on clinical decision making, without the aid of biological parameters, rendering selection of optimal treatment strategies difficult. Ultimately, there are no objective tools to predict or monitor treatment response. There are no means of sub-stratifying patients based on distinct differences in the underlying disease phenotype. Treatment may have differential effects on distinct molecular etiologies and it is essential to determine whether such differences can be identified before treatment initiation. This would reduce the time to remission, prevent recurrence and side effects, and improve the long term outcome.

Therefore, there is an urgent clinical need to identify objective molecular biomarkers which predict antidepressant treatment response. Such an approach would enable identification of responders and non-responders prior to treatment initiation. It would promote a more informed choice of antidepressant medication and reduce unnecessary drug-exposure and side effects for the non-responders. The healthcare system and the clinical development of novel drugs would benefit by cutting costs regarding the large group of non-responders. The current work aims to develop molecular tools that can be used to optimize the prediction and monitoring of responses to antidepressant treatment.

SUMMARY OF THE INVENTION

According to a first aspect of the invention, there is provided the use of ApoA-IV as a biomarker to predict whether a patient will respond to antidepressant treatment.

According to a further aspect of the invention, there is provided a method of predicting whether a patient will respond to antidepressant treatment, comprising:
(a) obtaining a biological sample from a patient;
(b) quantifying the amount of ApoA-IV in the biological sample;
(c) comparing the amount of ApoA-IV in the biological sample with the amount present in one or more reference samples obtained from one or more responders to antidepressant treatment and/or one or more reference samples obtained from one or more non-responders to antidepressant treatment, such that
(i) an equivalent level of ApoA-IV in the test biological sample compared with the reference sample(s) from responders; or
(ii) a difference in the level of ApoA-IV in the test biological sample compared with the reference sample(s) from non-responders, is indicative of whether the patient will respond to antidepressant treatment.

According to a further aspect of the invention, there is provided a method of monitoring efficacy of an antidepressant treatment in a patient having, suspected of having, or of being predisposed to major depressive disorder, comprising:
(a) obtaining a biological sample from a patient;
(b) quantifying the amount of ApoA-IV in the biological sample;
(c) comparing the amount of ApoA-IV in the biological sample with the amount present in one or more biological samples taken on another occasion from the patient, such that a difference in the level of ApoA-IV in the biological sample is indicative of the efficacy of an antidepressant treatment.

A further aspect of the invention provides ligands, such as naturally occurring or chemically synthesised compounds, capable of specific binding to the peptide biomarker. A ligand according to the invention may comprise a peptide, an antibody or a fragment thereof, or an aptamer or oligonucleotide, capable of specific binding to the peptide biomarker. The antibody can be a monoclonal antibody or a fragment thereof capable of specific binding to the peptide biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the peptide biomarker or a structural/shape mimic thereof capable of specific binding to an antibody against the peptide biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the peptide. In these uses, the detection and/or quantification can be performed on a biological sample such as from the group consisting of CSF, whole blood, blood serum, plasma, urine, saliva, or other bodily fluid, breath, e.g. as condensed breath, or an extract or purification therefrom, or dilution thereof.

Diagnostic or monitoring kits are provided for performing methods of the invention. Such kits will suitably comprise a ligand according to the invention, for detection and/or quantification of the peptide biomarker, and/or a biosensor, and/or an array as described herein, optionally together with instructions for use of the kit.

A further aspect of the invention provides a kit comprising reagents and/or a biosensor capable of detecting and/or quantifying ApoA-IV, for use in predicting whether a patient will respond to antidepressant treatment.

DETAILED DESCRIPTION OF THE INVENTION

Figure 1:
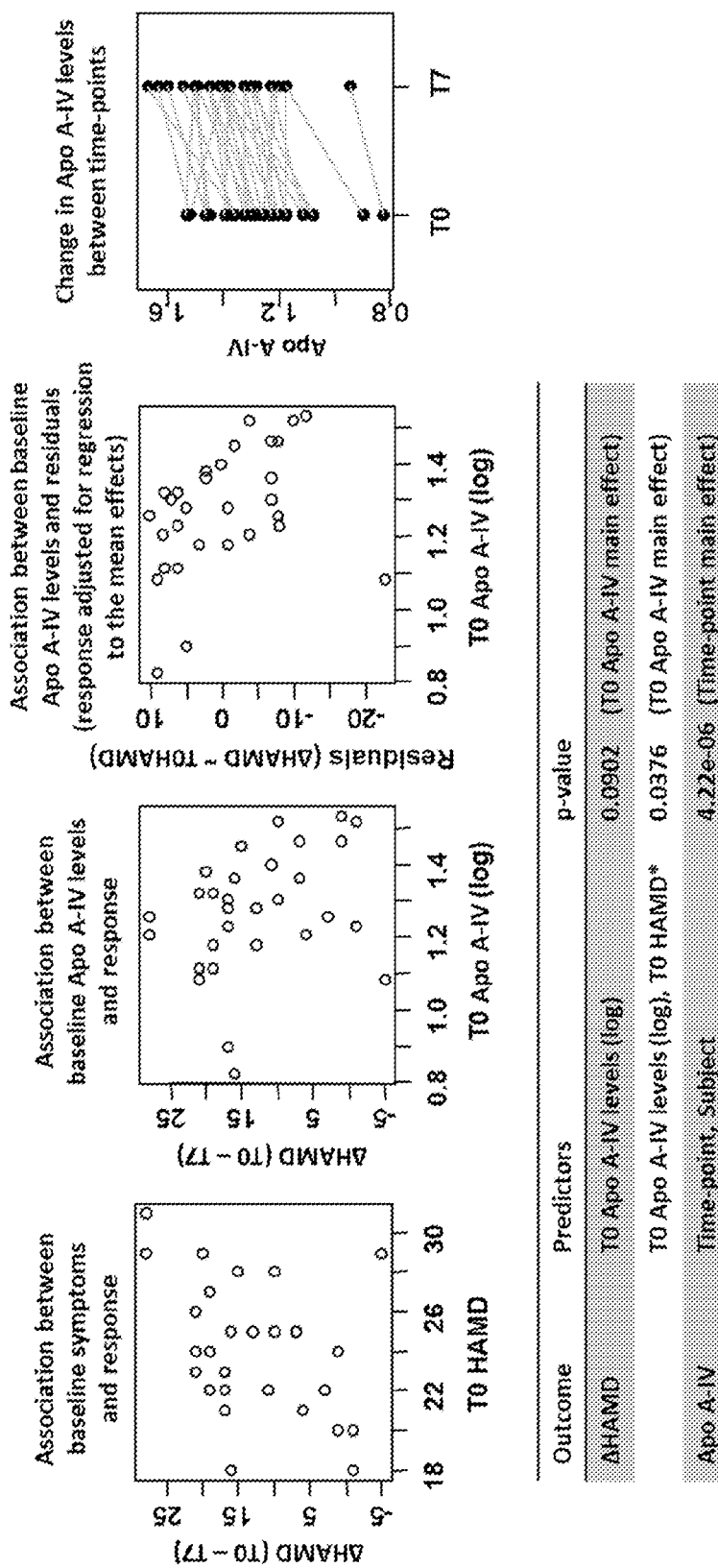
FIG. 1: Association between baseline ApoA-IV levels and response to venlafaxine treatment in cohort 1. Plots from left to right: T0 HAMD vs ΔHAMD (T0-T7) plot illustrates the "Regression to the mean effect" whereby baseline symptom severity (T0 HAMD) was significantly associated with response (ΔHAMD) to treatment; T0 ApoA-IV (log) vs ΔHAMD (T0-T7) plot shows a weak association between the baseline ApoA-IV levels and response to venlafaxine treatment; T0 ApoA-IV (log) vs regression residuals (ΔHAMD~T0 HAMD) plot shows a significant association between baseline ApoA-IV levels and response after adjusting for the "Regression to the mean effect" (T0 HAMD as covariate); change in ApoA-IV levels between time-points plot illustrates a significant increase in ApoA-IV levels following treatment by week 7 (T7). The embedded table shows the main effects of ApoA-IV on response to treatment before and after accounting for the "Regression to the mean effect" along with the main effect of time-point (baseline to endpoint) on serum ApoA-IV levels.

According to a first aspect of the invention, there is provided the use of ApoA-IV as a biomarker to predict whether a patient will respond to antidepressant treatment.

The findings described herein highlight the potential of ApoA-IV to be used as part of a blood based test in the clinic to identify responders and non-responders prior to treatment initiation. Such a test would be an important breakthrough in the field of psychiatry. It would aid clinical decision making, help to identify the best treatment approach for each patient and subsequently reduce the risk of recurrence/relapses and side effects, and improve the long term outcome.

References herein to "ApoA-IV" or "ApoA4" refer to the plasma protein Apolipoprotein A-IV. This protein is part of the family of human apolipoproteins which are involved in binding and transporting lipids as lipoproteins. There are several known classes of apolipoproteins (i.e. A, B, C, D, E and H) which may be further categorised into sub-classes (e.g. A-I, A-II, A-IV and A-V).

The term "biomarker" means a distinctive biological or biologically derived indicator of a process, event, or condition. Peptide biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

A patient will be considered to "respond" to treatment if the Hamilton Depression Rating Scale (HAMD) sum score is reduced by at least 50%, for example 55%, 60%, 65%, 70%, 75%, 80%, 85%, 90%, 95% or 100%. The Hamilton Depression Rating Scale provides an indication of the severity of depression by scoring answers from a series of set questions. A score of 0-7 is considered to be normal while scores of 20 or higher indicate moderate, severe, or very severe depression (Hamilton M. (1960) *J. Neurol. Neurosurg. Psychiatry* 23:56-62). A patient with a HAMD sum score of less than 7 is considered to be in remission (i.e. absence of the disease).

It will be apparent that a patient will be considered to not respond to treatment if their HAMD score is not reduced by more than 50%.

Use of the biomarker defined herein will be able to identify which patients will successfully respond to antidepressant treatments. This will save the costs of futile therapy in non-responding patients. Patients would also benefit from a personalised treatment approach, better clinical outcome and better compliance. For the medical staff it would be a very useful tool to better tailor treatment to individual patient needs and to help with long term monitoring.

In one embodiment, the patient is diagnosed with Major Depressive Disorder (MDD). In a further embodiment, the patient is a recurrent Major Depressive Disorder patient. In a yet further embodiment, the patient is a first onset drug naïve Major Depressive Disorder patient.

Major depressive disorder is a mental disorder characterized by a pervasive low mood, low self-esteem, and loss of interest or pleasure in normally enjoyable activities. The term "major depressive disorder" (which is also known as clinical depression, major depression, unipolar depression, or unipolar disorder) was selected by the American Psychiatric Association for this symptom cluster under mood disorders in the 1980 version of the Diagnostic and Statistical Manual of Mental Disorders (DSM-IV) classification, and has become widely used since.

In one embodiment, the antidepressant treatment is selected from: venlafaxine, imipramine, agomelatin, amitriptillin, cipralex, citalopram, doxepin, duloxetine, lithium, lorazepam, lormetazepam, mirtazapine, opipramol, paroxetine, reboxetin, remergil, risperidone, seroquel, sertraline, trancylcypromin, trimiparine, trimipramine, fluoxetine, escitalopram or a combination thereof.

References herein to "antidepressant treatment" or "antidepressant therapy" refer to medications used for the treatment of depression. The invention described herein provides a means for clinicians to identify patients that will benefit from antidepressant medication which will save time in finding the most appropriate and effective treatment for the patient.

According to a further aspect of the invention, there is provided a method of predicting whether a patient will respond to antidepressant treatment, comprising:

(a) obtaining a biological sample from a patient;
(b) quantifying the amount of ApoA-IV in the biological sample;
(c) comparing the amount of ApoA-IV in the biological sample with the amount present in one or more reference samples obtained from one or more responders to antidepressant treatment and/or one or more reference samples obtained from one or more non-responders to antidepressant treatment, such that
(i) an equivalent level of ApoA-IV in the test biological sample compared with the reference sample(s) from responders; or
(ii) a difference in the level of ApoA-IV in the test biological sample compared with the reference sample(s) from non-responders, is indicative of whether the patient will respond to antidepressant treatment.

References herein to "responder" refer to an individual who has demonstrated a response to antidepressant treatment. References herein to "non-responder" refer to an individual who has not demonstrated a response to antidepressant treatment.

It should be noted that references to biomarker amounts or levels also include references to a biomarker range.

It will be appreciated that references herein to "difference in the level" refer to either a higher or lower level of ApoA-IV in the test biological sample compared with the reference sample(s) from non-responders.

The inventors have made the surprising discovery that a lower level (i.e. a decrease) of ApoA-IV in the test biological sample compared with the one or more reference samples obtained from one or more non-responders to antidepressant treatment is indicative that the patient will respond to antidepressant treatment. In particular, the lower level is a lower baseline or pre-treatment level of ApoA-IV.

In one embodiment, the lower level is a <1 fold difference relative to the reference sample, such as a fold difference of 0.9, 0.8, 0.7, 0.6, 0.5, 0.4, 0.3, 0.2, 0.1, 0.05, 0.01 or any ranges therebetween. In one embodiment, the lower level is between a 0.1 and 0.85 fold difference relative to the reference sample, such as between a 0.2 and 0.7 fold difference relative to the reference sample. In a further embodiment, the lower level is between a 0.25 and 0.75 fold difference relative to the reference sample.

In one embodiment, the higher level is a >1 fold difference relative to the reference sample, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges therebetween. In one embodiment, the higher level is between a 1 and 15 fold difference relative to the reference sample, such as between a 1.5 and 12 fold difference relative to the reference sample. In a further embodiment, the higher level is between a 1 and 7 fold difference relative to the reference sample.

In one embodiment, the equivalent level is the same or a similar level of ApoA-IV in the test biological sample compared with the reference sample(s) from an individual that responds to antidepressant therapy.

References herein to the "same" level of biomarker indicate that the level of biomarker measured in each sample is identical (i.e. when compared to the selected reference). References herein to a "similar" level of biomarker indicate that levels are not identical but the difference between them is not statistically significant (i.e. the levels have comparable quantities).

As used herein, the term "biosensor" means anything capable of detecting the presence of the biomarker. Examples of biosensors are described herein.

In one embodiment, the biomarker defined herein may be replaced by a molecule, or a measurable fragment of the molecule, found upstream or downstream of the biomarker in a biological pathway.

Biosensors according to the invention may comprise a ligand or ligands, as described herein, capable of specific binding to the peptide biomarker. Such biosensors are useful in detecting and/or quantifying a peptide of the invention.

Kits for the monitoring of antidepressant treatment response are described herein. In one embodiment, the kits additionally contain a biosensor capable of detecting and/or quantifying a peptide biomarker.

Also provided is a method of monitoring efficacy of a therapy for major depressive disorder in a subject having such a disorder, suspected of having such a disorder, or of being predisposed thereto, comprising detecting and/or quantifying the peptide present in a biological sample from said subject. In monitoring methods, test samples may be taken on two or more occasions. The method may further comprise comparing the level of the biomarker present in the test sample with one or more reference(s) and/or with one or more previous test sample(s) taken earlier from the same test subject, e.g. prior to commencement of therapy, and/or from the same test subject at an earlier stage of therapy. The method may comprise detecting a change in the level of the biomarker in test samples taken on different occasions.

According to a further aspect of the invention, there is provided a method of monitoring efficacy of an antidepressant treatment in a patient having, suspected of having, or of being predisposed to major depressive disorder, comprising:
  (a) obtaining a biological sample from a patient;
  (b) quantifying the amount of ApoA-IV in the biological sample;
  (c) comparing the amount of ApoA-IV in the biological sample with the amount present in one or more biological samples taken on another occasion from the patient, such that a difference in the level of ApoA-IV in the biological sample is indicative of the efficacy of an antidepressant treatment.

Alternatively, the invention provides a method for monitoring efficacy of therapy for major depressive disorder in a subject, comprising:
  (a) quantifying the amount of ApoA-IV in a test sample; and
  (b) comparing the amount of ApoA-IV in said test sample with the amount present in one or more previous test sample(s) taken at an earlier time from the same test subject.

In one embodiment, the method comprises comparing the amount of ApoA-IV in said test biological sample with the amount present in one or more samples taken from said patient prior to commencement of treatment, and/or one or more samples taken from said patient during treatment.

The present inventors have made the surprising discovery that there is an increase in the level of ApoA-IV in one or more samples taken from said patient during treatment compared with the one or more samples taken from said patient prior to commencement of treatment. The increase in ApoA-IV levels following treatment suggests that this molecule is also targeted by antidepressant treatment.

For biomarkers which are increased in patients with major depressive disorder, a decrease in the level of the peptide biomarker in the test sample relative to the level in a previous test sample taken earlier from the same test subject is indicative of a beneficial effect, e.g. stabilisation or improvement, of said therapy on the disorder, suspected disorder or predisposition thereto. For biomarkers which are decreased in patients with major depressive disorder, an increase in the level of the peptide biomarker in the test sample relative to the level in a previous test sample taken earlier from the same test subject is indicative of a beneficial effect, e.g. stabilisation or improvement, of said therapy on the disorder, suspected disorder or predisposition thereto.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-depressant therapy. Samples can be taken at intervals over the remaining life, or a part thereof, of a subject.

Monitoring methods of the invention can be used to monitor onset, progression, stabilisation, amelioration and/or remission.

The term "detecting" as used herein means confirming the presence of the peptide biomarker present in the sample. Quantifying the amount of the biomarker present in a sample may include determining the concentration of the peptide biomarker present in the sample. Detecting and/or quantifying may be performed directly on the sample, or indirectly on an extract therefrom, or on a dilution thereof.

In alternative aspects of the invention, the presence of the peptide biomarker is assessed by detecting and/or quantifying antibody or fragments thereof capable of specific binding to the biomarker that are generated by the subject's body in response to the peptide and thus are present in a biological sample from a subject having major depressive disorder or a predisposition thereto.

Detecting and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the peptide biomarker in the sample or samples. Biological samples that may be tested in a method of the invention include cerebrospinal fluid (CSF), whole blood, blood serum, plasma, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

In one embodiment, the biological sample is whole blood, blood serum or plasma, such as blood serum.

Detection and/or quantification of peptide biomarkers may be performed by detection of the peptide biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker.

The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods according to the invention may comprise analysing a sample of blood serum by SELDI TOF or MALDI TOF to detect the presence or level of the peptide biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the peptide biomarkers may be performed using an immunological method, involving an antibody, or a fragment thereof capable of specific binding to the peptide biomarker. Suitable immunological methods include sandwich immunoassays, such as sandwich ELISA, in which the detection of the peptide biomarkers is performed using two antibodies which recognize different epitopes on a peptide biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate. However, these complexes will scatter incident light and this can be measured using a nephelometer. The antigen, i.e. biomarker, concentration can be determined within minutes of the reaction.

Radioimmunoassay (RIA) methods employ radioactive isotopes such as $I^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of EIA approaches that of RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of the peptide biomarker of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for a peptide biomarker of the invention may be immobilised on an avidin or streptavidin surface, the immobilised ligand may then be exposed to a sample containing or suspected of containing the peptide biomarker in order to detect and/or quantify a peptide biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and F(ab')$_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers, appropriate diagnostic tools such as biosensors can be developed, accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker, electrical, thermal, magnetic, optical (e.g. hologram) or acoustic technologies. Using such biosensors, it is possible to detect the target biomarker at the anticipated concentrations found in biological samples.

Thus, according to a further aspect of the invention there is provided an apparatus for monitoring major depressive disorder (MDD) or predicting a response to antidepressant treatment in MDD patients, which comprises a biosensor, microanalytical, microengineered, microseparation and/or immunochromatography system configured to detect and/or quantify the biomarker defined herein.

The biomarker of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarker of the invention.

Methods involving detection and/or quantification of the peptide biomarker of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

There is provided a method of identifying a substance capable of promoting or suppressing the generation of the peptide biomarker in a subject, comprising exposing a test cell to a test substance and monitoring the level of the peptide biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

The test substance can be a known chemical or pharmaceutical substance, such as, but not limited to, an antidepressive disorder therapeutic; or the test substance can be novel synthetic or natural chemical entity, or a combination of two or more of the aforesaid substances.

In methods for identifying substances of potential therapeutic use, non-human animals or cells can be used that are capable of expressing the peptide.

Screening methods also encompass a method of identifying a ligand capable of binding to the peptide biomarker according to the invention, comprising incubating a test substance in the presence of the peptide biomarker in conditions appropriate for binding, and detecting and/or quantifying binding of the peptide to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the peptide biomarker, or of suppressing generation of the peptide biomarker. The term "substances" includes substances that do not directly bind the peptide biomarker and directly modulate a function, but instead indirectly modulate a function of the peptide biomarker. Ligands are also included in the term substances; ligands of the invention (e.g. a natural or synthetic chemical compound, peptide, aptamer, oligonucleotide, antibody or antibody fragment) are capable of binding, suitably specific binding, to the peptide.

The invention further provides a substance according to the invention for use in the treatment of major depressive disorder, or predisposition thereto.

In one embodiment, the method additionally comprises administering an antidepressant to a patient predicted to respond to antidepressant treatment. Thus, according to a further aspect of the invention, there is provided a method of treating a patient suffering with depression, comprising:

(a) obtaining a biological sample from a patient;

(b) quantifying the amount of ApoA-IV in the biological sample;

(c) comparing the amount of ApoA-IV in the biological sample with the amount present in one or more reference samples obtained from one or more responders to antidepressant treatment and/or one or more reference samples obtained from one or more non-responders to antidepressant treatment, such that (i) an equivalent level of ApoA-IV in the test biological sample compared with the reference sample(s) from responders; or (ii) a difference in the level of ApoA-IV in the test biological sample compared with the reference sample(s) from non-responders, is indicative of whether the patient will respond to antidepressant treatment; and (d) administering an antidepressant to a patient predicted to respond to antidepressant treatment.

It will be appreciated that each of the embodiments for the method of predicting and method of monitoring efficacy aspects of the invention apply equally to this method of treatment aspect of the invention.

Also provided is the use of a substance according to the invention in the treatment of major depressive disorder, or predisposition thereto.

Also provided is the use of a substance according to the invention as a medicament.

A further aspect of the invention provides a kit comprising reagents and/or a biosensor capable of detecting and/or quantifying ApoA-IV, for use in predicting whether a patient will respond to antidepressant treatment. Suitably a kit according to the invention may contain one or more components selected from the group: a ligand specific for the peptide biomarker or a structural/shape mimic of the peptide biomarker, one or more controls, one or more reagents and one or more consumables; optionally together with instructions for use of the kit in accordance with any of the methods defined herein.

The biomarker of the invention is useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient. The biomarker can thus be used to titrate the optimal dose, predict a positive therapeutic response and identify those patients at high risk of severe side effects.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarker is sensitive to the state of the disorder, it provides an indication of the impact of drug therapy or of substance abuse.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. The reference standard used for any embodiment disclosed herein may comprise average, mean, or median levels of the one or more analyte biomarkers or the levels of the specific panel of analyte biomarkers in a control population. The reference standard may additionally comprise cutoff values or any other statistical attribute of the control population, such as a standard deviation from the mean levels of the one or more analyte biomarkers or the levels of the specific panel of analyte biomarkers.

In some embodiments, comparing the level of the one or more analyte biomarkers is performed using a cutoff value. In related embodiments, if the level of the one or more analyte biomarkers is greater than the cutoff value, the individual may be diagnosed as having, or being at risk of developing depression. In other distinct embodiments, if the level of the one or more analyte biomarkers is less than the cutoff value, the individual may be diagnosed as having, or being at risk of developing depression. Cutoff values may be determined by statistical analysis of the control population to determine which levels represent a high likelihood that an individual does or does not belong to the control population. In some embodiments, comparing the level of the one or more analyte biomarkers is performed using other statistical methods. In related embodiments, comparing comprises logistic or linear regression. In other embodiments, comparing comprises computing an odds ratio.

In some embodiments, the control population may comprise healthy individuals, individuals with depression, or a mixed population of individuals with depression.

In some embodiments, individuals with levels of one or more analyte biomarkers or levels of a specific panel of analyte biomarkers greater than the reference levels would be more likely to have depression. Therefore, an individual presenting with levels of the one or more analyte biomarkers or levels of the specific panel of analyte biomarkers greater than the reference standard would be a candidate for treatment with antidepressant therapy, or with more aggressive therapy. On the other hand, an individual presenting with levels of the one or more analyte biomarkers or levels of the specific panel of analyte biomarkers less than or equal to the reference standard would be less likely to have depression and therefore be a candidate for no antidepressant therapy, delayed antidepressant therapy or less aggressive antidepressant therapy.

In other embodiments, individuals with levels of one or more analyte biomarkers or levels of a specific panel of analyte biomarkers less than the reference levels would be more likely to have depression. Therefore, an individual presenting with levels of the one or more analyte biomarkers or levels of the specific panel of analyte biomarkers less than the reference standard would be a candidate for treatment with antidepressant therapy, or with more aggressive therapy. On the other hand, an individual presenting with levels of the one or more analyte biomarkers or levels of the specific panel of analyte biomarkers greater than or equal to the reference standard would be less likely to have depression and therefore be a candidate for no antidepressant therapy, delayed antidepressant therapy or less aggressive antidepressant therapy.

Reference Therapy for Treatment

In some embodiments, a patient is treated more or less aggressively than a reference therapy. A reference therapy is any therapy that is the standard of care for depression. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Depression

Health practitioners treat depression by taking actions to ameliorate the causes or symptoms of the disorder in a patient. Treatment may comprise drug-based or non-drug-based therapies.

Drug-based therapies may include: selecting and administering one or more antidepressant drugs to the patient, adjusting the dosage of an antidepressant drug, adjusting the dosing schedule of an antidepressant drug, and adjusting the length of the therapy with an antidepressant drug. Antidepressant drugs are selected by practitioners based on the nature of the symptoms and the patient's response to any previous treatments. The dosage of an antidepressant drug can be adjusted as well by the practitioner based on the nature of the drug, the nature of the patient's symptoms, the patient's response to previous treatment, and the patient's response to the drug. The dosing schedule can also be adjusted by the practitioner based on the nature of the drug, the nature of the patient's symptoms, the patient's response to previous treatment, and the patient's response to the drug. Also, the length of the therapy can be adjusted by the practitioner based on the nature of the drug, the nature of the patient's symptoms, the patient's response to previous treatment, and the patient's response to the drug. Additionally, the practitioner can select between a single drug therapy, a dual drug therapy, or a triple drug therapy. In some embodiments, a practitioner may optionally treat the patient with a combination of one or more antidepressant drugs and one or more non-drug-based therapies.

In one embodiment, the practitioner begins antidepressant therapy based on a comparison between a reference level and the levels of one or more analyte biomarkers or the levels of a specific panel of analyte biomarkers in a sample from a patient. In one embodiment, therapy comprises the selection and administration of an antidepressant drug to the patient by the practitioner. In another embodiment, therapy comprises the selection and administration of two antidepressant drugs to the patient by the practitioner as part of dual therapy. In another embodiment, therapy comprises the selection and administration of three antidepressant drugs to the patient by the practitioner as part of triple therapy.

Antidepressant drugs are commonly used by medical practitioners, and a skilled person may identify the appropriate antidepressant drug to administer based on the medical literature. In some embodiments, treatment comprises administering to an individual a selective serotonin reuptake inhibitor ("SSRI"). In some embodiments, the SSRI is citalopram. In some embodiments, the SSRI is escitalopram. In some embodiments, the SSRI is fluoxetine. In some embodiments, the SSRI is paroxetine. In some embodiments, the SSRI is sertraline.

In other embodiments, treatment comprises administering to an individual a serotonin-norepinephrine reuptake inhibitors ("SNRI"). In some embodiments, the SNRI is venlafaxine. In other embodiments, the SNRI is duloxetine.

In other embodiments, treatment comprises administering to an individual a norepinephrine and dopamine reuptake inhibitor ("NDRI"). In one embodiment, the NDRI is bupropion.

In other embodiments, treatment comprises administering to an individual a tetracyclic antidepressant ("tetracyclic"). In some embodiments, the tetracyclic is amoxapine. In some embodiments, the tetracyclic is maprotiline. In some embodiments, the tetracyclic is mazindol. In some embodiments, the tetracyclic is mirtazapine.

In other embodiments, treatment comprises administering to an individual a tricyclic antidepressant ("tricyclic"). In some embodiments, the tricyclic is amitriptyline. In some embodiments, the tricyclic is imipramine. In some embodiments, the tricyclic is nortriptyline.

In other embodiments, treatment comprises administering to an individual a monoamine oxidase inhibitor ("MAOI"). In some embodiments, the MAOI is selegiline. In some embodiments, the MAOI is isocarboxazid. In some embodiments, the MAOI is phenelzine. In some embodiments, the MAOI is tranylcypromine.

In addition to or in lieu of drug-based therapies, in some embodiments a practitioner may also treat an individual with non-drug-based antidepressant therapies. In some embodiments, the non-drug based therapy comprises cognitive-behavioral therapy. In some embodiments, the non-drug based therapy comprises psychotherapy. In a related embodiment, the non-drug based therapy comprises psychodynamic therapy. In some embodiments, the non-drug based therapy comprises electroconvulsive therapy. In some embodiments, the non-drug based therapy comprises hospitalization and residential treatment programs. In some embodiments, the non-drug based therapy comprises vagus nerve stimulation. In some embodiments, the non-drug based therapy comprises transcranial magnetic stimulation. In some embodiments, the non-drug based therapy comprises regular, vigorous exercise.

In one embodiment, the practitioner adjusts the antidepressant therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. In one embodiment a less aggressive therapy comprises delaying treatment. In one embodiment a less aggressive therapy comprises selecting and administering less potent drugs. In one embodiment a less aggressive therapy comprises decreasing dosage of antidepressant drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises earlier administration of antidepressant drugs. In one embodiment a more aggressive therapy comprises increased dosage of antidepressant drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Systems for Diagnosing and Treating Depression

The results of any analyses according to the invention will often be communicated to physicians and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. The statements and visual forms can be recorded on a tangible medium such as papers, computer readable media such as hard disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on levels of one or more analyte biomarkers or levels of a specific panel of analyte biomarkers for at least one patient sample. The method comprises the steps of (1) determining levels of one or more analyte biomarkers or levels of a specific panel of analyte biomarkers for at least one patient sample according to methods of the present invention; and (2) embodying the result of the determining step in a transmittable form. The transmittable form is the product of such a method.

Techniques for analyzing levels of one or more analyte biomarkers or levels of a specific panel of analyte biomarkers for at least one patient sample will often be implemented using hardware, software or a combination thereof in one or more computer systems or other processing systems capable of effectuating such analysis.

Thus, the present invention further provides a system for determining whether an individual suffers from depression, comprising: (1) a sample analyzer for determining the levels of one or more analyte biomarkers or levels of a specific panel of analyte biomarkers for at least one patient sample, wherein the sample analyzer contains the patient sample; (2) a first computer program for (a) receiving data regarding the levels of one or more analyte biomarkers or the levels of a specific panel of analyte biomarkers; and optionally (3) a second computer program for comparing the test value to one or more reference standards each associated with a predetermined degree of risk of depression.

The sample analyzer can be any instruments useful in determining the levels of biomarkers in a sample, as described herein.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out disease risk analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present invention provides a system for determining whether a patient has depression. Generally speaking, the system comprises (1) computer program for receiving, storing, and/or retrieving data regarding levels of biomarkers in a patient's sample and optionally clinical parameter data (e.g., disease-related symptoms); (2) computer program for querying this patient data; (3) computer program for concluding whether an individual suffers from depression based on this patient data; and optionally (4) computer program for outputting/displaying this conclusion. In some embodiments this computer program for outputting the conclusion may comprise a computer program for informing a health care professional of the conclusion The practice of the present invention may also employ conventional biology methods, software and systems. Computer software products of the invention typically include computer readable media having computer-executable Instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, Ser No. 61/793,031 Page 38 of 64 BIOINFORMATICS: A PRACTICAL GUIDE FOR ANALYSIS OF GENE AND PROTEINS (Wiley & Sons, Inc., 2nd ed., 2001); see also, U.S. Pat. No. 6,420,108.

Computing Device

Figure 5:
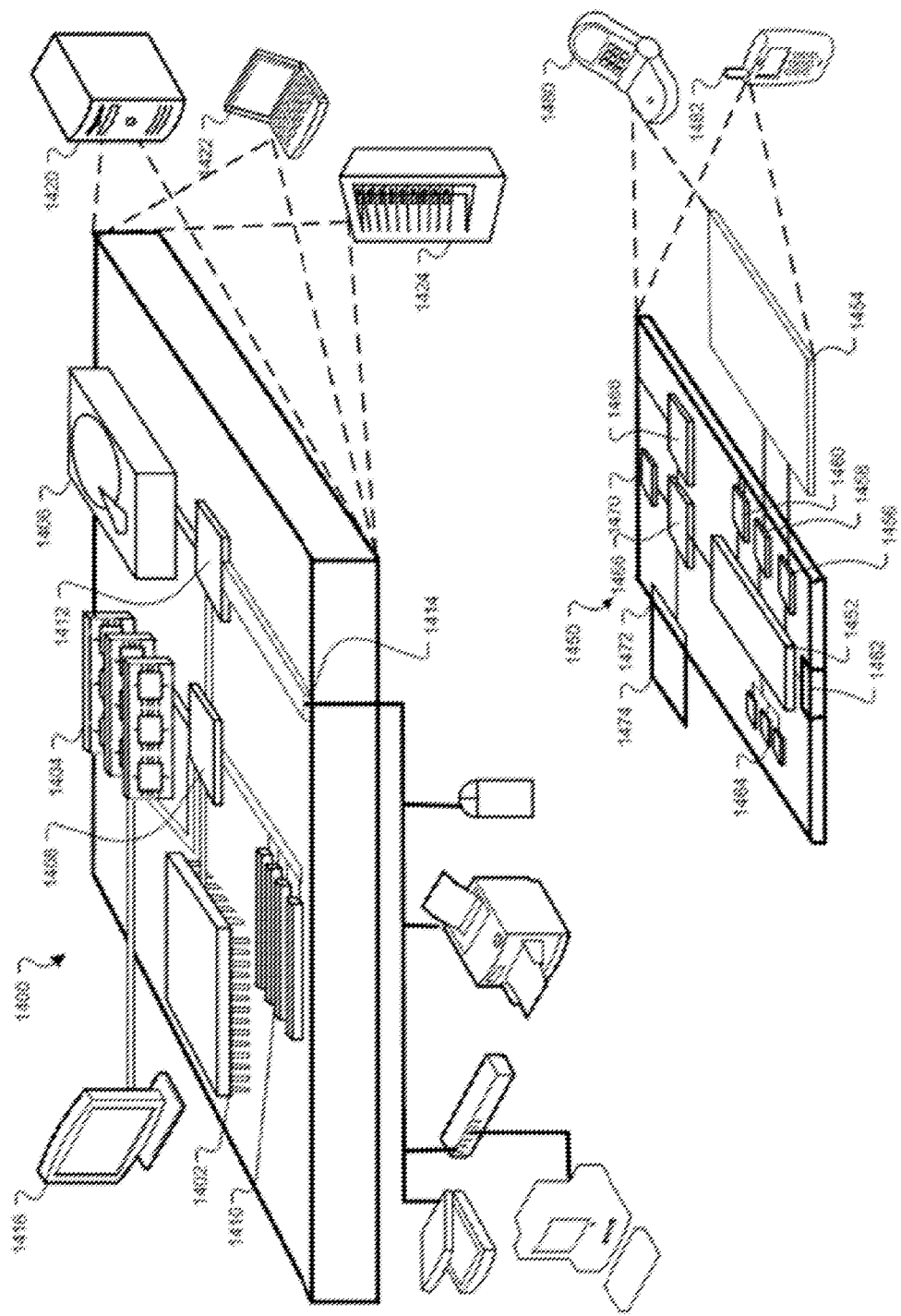
FIG. 5: A schematic representation of a computer device and a mobile computer device which may be used with the techniques described herein.

FIG. 5 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary.

Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a computing system provided herein can be configured to include one or more sample analyzers. A sample analyzer can be configured to produce a signal or a plurality of signals that quantify amounts of a biomarker, such as ApoA-IV, in a biological sample. The computing device can further be configured to compare the amount of a biomarker, such as ApoA-IV in the biological sample with the amount present in one or more reference samples obtained from one or more responders to antidepressant treatment and/or one or more reference samples obtained from one or more non-responders to antidepressant treatment. The computing device can further determine a difference in the level of a biomarker, such as ApoA-IV compared with a reference sample or samples from non-responders. The will allow the computer device to provide an output that indicates whether the patient will respond to an antidepressant treatment, or to determine the efficacy of an antidepressant treatment.

The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer. In some cases, a computing system provided herein can include computer-executable instructions or a computer program (e.g., software) containing computer-executable instructions for formatting an output.

In some cases, a computing system provided herein can include a pre-processing device configured to process a sample (e.g., cancer cells) such that an expression-based assay can be performed. Examples of pre-processing devices include, without limitation, devices configured to enrich cell populations for cancer cells as opposed to non-cancer cells, devices configured to lyse cells and/or extract protein or genomic nucleic acid, and devices configured to enrich a sample for particular proteins or genomic DNA fragments.

The following studies illustrate the invention.

Methods

Clinical Samples

The study protocols were approved by the institutional ethical committee of the University of Magdeburg, Muenster, University Medical Centre, Mainz and the ethical review board of the Erasmus Medical centre, Rotterdam. All diagnoses and clinical tests were performed by psychiatrists under Good Clinical Practice-compliance to minimize variability. Informed written consent was given by all participants and all the studies were conducted according to the Declaration of Helsinki. All diagnoses were carried out using the Diagnostic and Statistical Manual (DSM)-IV for a unipolar major depressive episode. Cohort 1 was from the Erasmus Medical centre Rotterdam, The Netherlands, cohort 2 from the University of Magdeburg (Germany), cohort 3 was from the University of Muenster (Germany) and cohort 4 was from the University Medical Centre, Mainz, Germany. Severity of depressive symptoms was assessed at baseline prior to start of medication and at a follow-up time point. See Table 1 for the demographic details of the MDD patients from each cohort. Blood samples were collected from all subjects into S-Monovette 7.5 mL serum tubes (Sarstedt; Numbrecht, Germany) and serum prepared and stored at −80° C. in Low Binding Eppendorf tubes (Hamburg, Germany).

TABLE 1

Demographics overview

| Patients characteristics | Cohort 1 | Cohort 2 | Cohort 3 | Cohort 4 |
|---|---|---|---|---|
| n | 30 | 38 | 25 | 38 |
| Age (years) | 54 | 43 | 42 | 45 |
| Gender (M/F) | 15/15 | 15/22 | 7/14 | 19/19 |
| T0 BMI | 23 | 25 | Unknown | 26 |
| No. previous episodes (0/1/≥2/unknown) | 10/11/9/0 | 27/0/0/11 | 0/0/0/21 | 7/11/20/0 |
| Previous medication (Y/N) | 23/7 | 11/27 | 21/0 | 31/7 |
| Study antidepressant | Venlafaxine | Mixed | Mixed | Mixed |
| Patient status | inpatients | outpatients | outpatients | outpatients |
| Average baseline HAMD sum score | 24 | 22 | 28 | 21 |
| Average endpoint HAMD sum score | 11 | 7 | 7 | 13 |
| Time-point of assessment: | | | | |
| Baseline (T0) | T0 | T0 | T0 | T0 |
| Endpoint (Tep) | Tweek7 | Tweek6 | Tmonth2.5 | Tweek3-6 |
| Response status by endpoint (%) | | | | |
| Response (response/non-response) | 63 (19/30) | 84 (32/38) | 95 (20/21) | 10 (4/38) |
| Remission (remission/non-remission) | 40 (12/30) | 50 (19/38) | 43 (9/21) | 21 (8/38) |

Treatment response defined as Hamilton Depression Rating Scale (HAMD) sum score reduction (T0 to Tep) of ≥50% for the responders.

Remission defined as Tep HAMD sum score of <7 for the remitters.

Multiplexed Immunoassay

Approximately 250 analytes were measured in sera from patients in cohorts 1, 2, and 4 using the HumanMAP® multiplexed antigen immunoassays in a CLIA-certified laboratory at Rules Based Medicine. All samples were randomized and blinded to analysts using code numbers until all biochemical assays were complete to avoid any sequential bias due to the diagnosis, age and gender. Assays were calibrated using duplicate standard curves, raw intensity measurements converted to absolute protein concentrations using proprietary software, and instrument performance was verified using quality control samples. The protocol for the study participants, clinical samples and test methods was carried out in compliance with the Standards for Reporting of Diagnostic Accuracy (STARD) initiative.

Data analyses were performed using the statistical software package R (http://www.r-project.org).

Liquid-Chromatography Mass Spectrometry (LC-MSE)

Patient sera from cohort 3 were processed in random order and depleted of the 14 most abundant proteins using MARS14 (Agilent; Santa Clara, Calif., USA) on an ÄKTA™ purifier UPC 10 chromatography system (GE Healthcare; Little Chalfont, Bucks, UK) as reported previously (Levin et al., 2010). LC-MSE profiling was performed in expression mode using a Waters quadrupole time-of-flight (QToF) Premier mass spectrometer, as described previously (Levin et al., 2007). Data were processed using the Protein-Lynx Global Server (PLGS) v.2.3 (Waters) and Rosetta Inpharmatics Biosoftware Elucidator v3.3 (Seattle, Wash., USA) (Krishnamurthy et al., 2011). The human Swiss-Prot database (v57, 20,332 entries) search was performed using PLGS with the ion accounting algorithm described previously (Li et al., 2009). The subsequent protein identification criteria employed were described previously (Stelzhammer et al., 2012).

Results

This study attempted to identify baseline serum biomarkers which can predict response to antidepressant treatment by study endpoint (Tep). This was determined by examining associations between the baseline molecule levels in samples and the absolute change in symptom severity between baseline and endpoint (i.e. response by change in HAMD score [ΔHAMD]) as well as the change in the molecule levels following treatment. For all the analyses, results were adjusted for the confounding effects of T0 HAMD or baseline symptom severity ("Regression to the mean effect"), age and gender. The HumanMAP® Multi-Analyte Profiling platform (Myriad-RBM) was used to analyze approximately 250 proteins in serum samples from a total of 131 patients diagnosed with major depressive disorder recruited from psychiatric centres in Germany and Holland. Most of the recruited patients were recurrent and severely depressed at baseline assessment. The exception was cohort 2, where the majority of patients (27 out of 38) were first onset and drug naïve at baseline admission.

Figure 2:
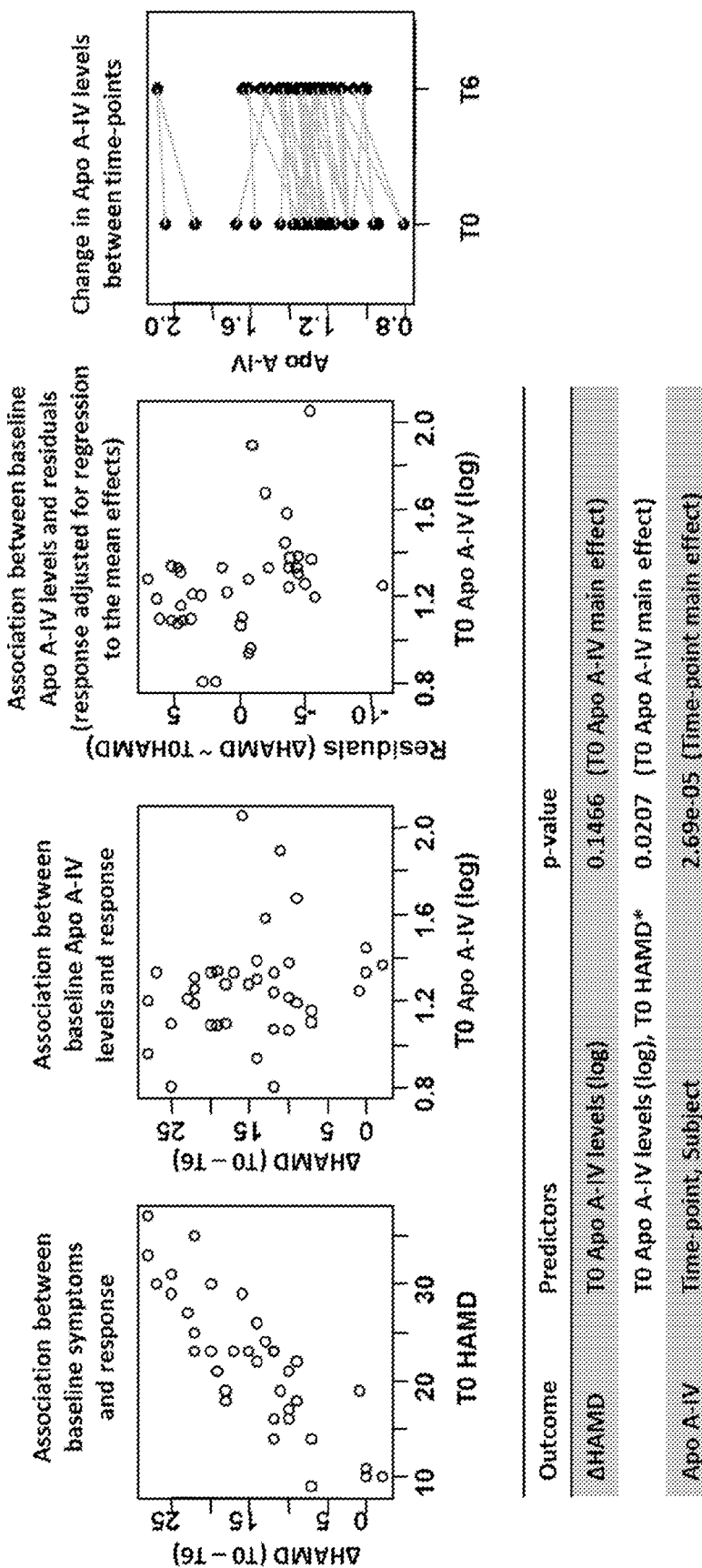
FIG. 2: Association between baseline ApoA-IV levels and response to mixed antidepressant treatment in cohort 2. Plots from left to right: T0 HAMD vs ΔHAMD (T0-T6) plot illustrates the "Regression to the mean effect" whereby baseline symptom severity (T0 HAMD) was significantly associated with response (ΔHAMD) to treatment; T0 ApoA-IV (log) vs ΔHAMD (T0-T6) plot shows a weak association between the baseline ApoA-IV levels and response to mixed antidepressant treatment; T0 ApoA-IV (log) vs regression residuals (ΔHAMD~T0 HAMD) plot shows a significant association between baseline ApoA-IV levels and response after adjusting for the "Regression to the mean effect" (T0 HAMD as covariate); change in ApoA-IV levels between time-points plot illustrates a significant increase in ApoA-IV levels following treatment by week 6 (T6). The embedded table shows the main effects of ApoA-IV on response to treatment before and after accounting for the "Regression to the mean effect" along with the main effect of time-point (baseline to endpoint) on serum ApoA-IV levels.
Figure 3:
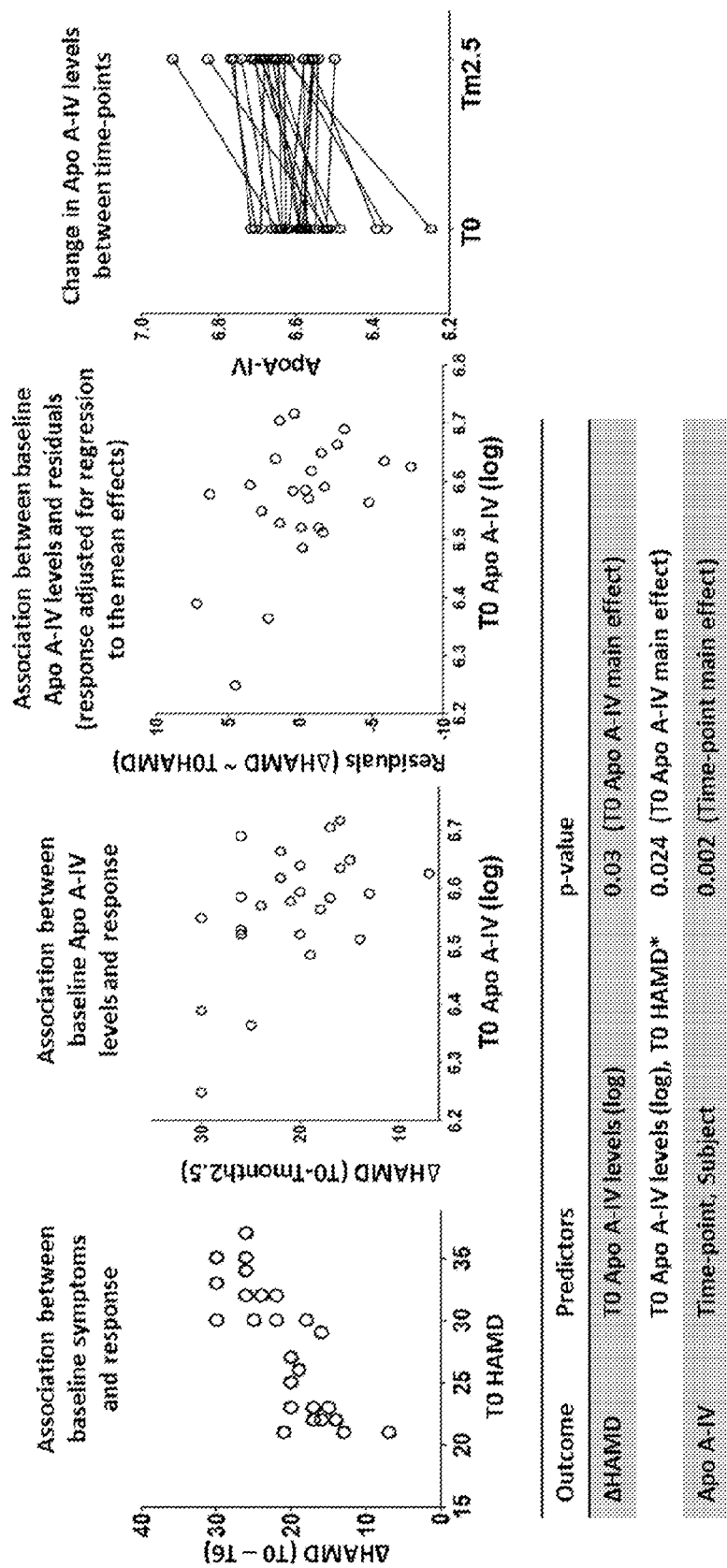
FIG. 3: Association between baseline ApoA-IV levels and response to mixed antidepressant treatment in cohort 3. Plots from left to right: T0 HAMD vs ΔHAMD (T0-Tm2.5) plot illustrates the "Regression to the mean effect" whereby baseline symptom severity (T0 HAMD) was significantly associated with response (ΔHAMD) to treatment; T0 ApoA-IV vs ΔHAMD (T0-Tm2.5) plot shows a significant association between the baseline ApoA-IV levels and response to mixed antidepressant treatment; T0 ApoA-IV vs regression residuals (ΔHAMD~T0 HAMD) plot shows a significant association between baseline ApoA-IV levels and response after adjusting for the "Regression to the mean effect" (T0 HAMD as covariate); change in ApoA-IV levels between time-points plot illustrates a significant increase in ApoA-IV levels following treatment by month 2.5 (Tm2.5). The embedded table shows the main effects of ApoA-IV on response to treatment before and after accounting for the "Regression to the mean effect" along with the main effect of time-point (baseline to endpoint) on serum ApoA-IV levels.

A "Regression to the mean effect" was observed in cohorts 1, 2 and 3 as illustrated in FIGS. 1, 2 and 3 by plots showing the significant association between baseline symptom severity (T0 HAMD) and response (ΔHAMD) to treatment. This represents a natural phenomenon whereby the more severely depressed patients are the more likely they are to achieve higher response to treatment. Therefore, T0 HAMD was accounted for as an additional confounding covariate in subsequent analysis.

After adjusting for the "Regression to the mean effect", the association between baseline Apolipoprotein A-IV (ApoA-IV) levels and response to venlafaxine and mixed antidepressant treatments was found to be significant in cohorts 1, 2 and 3. This finding suggested that ApoA-IV represents a reproducible baseline predictor of response to antidepressant treatment in recurrent MDD patients and potentially first onset drug naive patients. It showed that the higher the baseline serum ApoA-IV levels, the less responsive the patients were to antidepressant treatment by study endpoint. This is illustrated by plots showing significant negative association between baseline ApoA-IV levels and the regression residuals (adjusted response) in FIGS. 1, 2 and 3. The embedded tables in these figures show the significant main effects of baseline ApoA-IV levels ($p<0.05$) on the outcome variable (response) after accounting for the "Regression to the mean effects". The influence of the "Regression to the mean effect" was found to be substantial as without accounting for such effect, the baseline ApoA-IV levels in patients were only found to be weakly associated with response to treatment in cohorts 1 and 2. This is illustrated by plots showing a weak association between baseline ApoA-IV levels and response to venlafaxine treatment in FIG. 1 and mixed antidepressant treatment in FIG. 2.

Serum ApoA-IV levels in patients were also found to be increased significantly following venlafaxine and mixed antidepressant treatment by endpoint (Tep) in all cohorts. This finding suggested a significant treatment effect on the levels of this protein in MDD patients (FIGS. 1-4: plots showing a significant change in ApoA-IV levels between time-points and the embedded tables showing significant main effects of time-point on the serum ApoA-IV levels (p<0.05).

Figure 4:
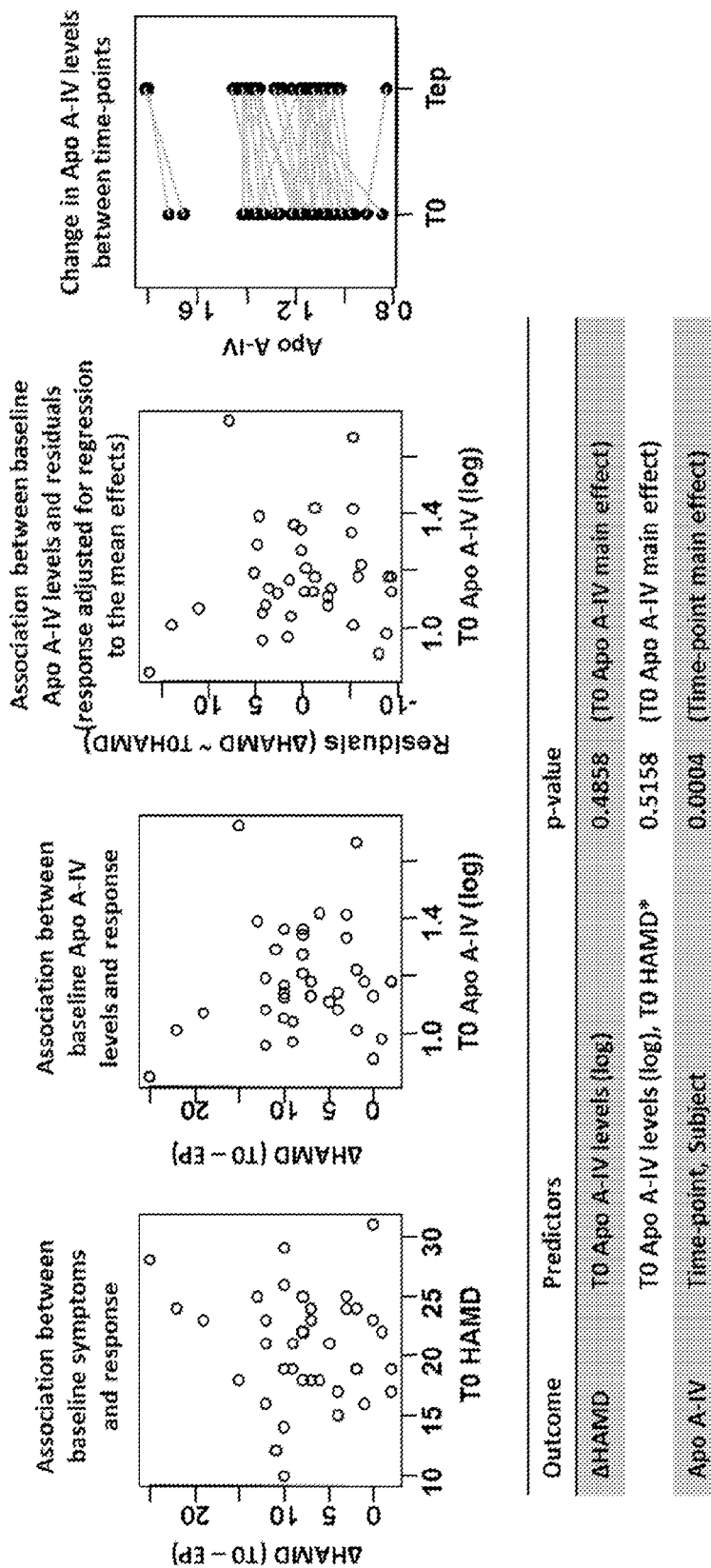
FIG. 4: Association between baseline ApoA-IV levels and response to mixed antidepressant treatment in cohort 4. Plots from left to right: T0 HAMD vs ΔHAMD (T0-Tep) plot shows that a "Regression to the mean effect" was not observed in this cohort; T0 ApoA-IV (log) vs ΔHAMD (T0-Tep) plot shows that there was no association between the baseline ApoA-IV levels and response to mixed antidepressant treatment; T0 ApoA-IV (log) vs regression residuals (ΔHAMD~T0 HAMD) plot shows that the association between baseline ApoA-IV levels and response remained non-significant even after accounting for the "Regression to the mean effect"; change in ApoA-IV levels between time-points plot illustrates a significant increase in ApoA-IV levels following treatment by the end-point (Tep). The embedded table shows the main effects of ApoA-IV on response to treatment before and after accounting for the "Regression to the mean effect" (T0 HAMD as covariate) along with the main effect of time-point (baseline to endpoint) on serum ApoA-IV levels.

Cohort 4 was the only case where baseline ApoA-IV levels were not found to be associated with response. A "Regression to the mean effect" was also not observed in this cohort. These findings may be attributed to the fact that only 10% of the MDD patients (4/38) in this cohort responded to mixed antidepressant treatment. Such response rate may have been too low to detect significant associations with the baseline ApoA-IV levels with sufficient statistical power. Nevertheless, consistent with the treatment induced changes observed in cohorts 1, 2 and 3, ApoA-IV levels in patients from this cohort were also found to be increased significantly following mixed antidepressant treatment (FIG. 4).

The invention claimed is:

1. A method for predicting whether a patient will respond to antidepressant treatment and treating the patient, comprising:
   (a) obtaining a biological sample from the patient;
   (b) quantifying the amount of ApoA-IV in the biological sample;
   (c) comparing the amount of ApoA-IV in the biological sample with the amount of ApoA-IV present in one or more reference samples obtained from one or more responders to antidepressant treatment and/or one or more reference samples obtained from one or more non-responders to antidepressant treatment, and identifying the patient as a responder to antidepressant treatment if:
      (i) the level of ApoA-IV in the biological sample is equivalent to the level of ApoA-IV in the one or more reference samples from the one or more responders; or
      (ii) the level of ApoA-IV in the biological sample is lower than the level of ApoA-IV in the one or more reference samples from the one or more non-responders, and
   (d) administering an anti-depressant to the patient identified as a responder patient.

2. The method according to claim 1, wherein the patient is identified as a responder patient to antidepressant treatment if the level of ApoA-IV in the test biological sample is lower than the level of ApoA-IV in the one or more reference samples obtained from the one or more non-responders to antidepressant.

3. The method according to claim 1, wherein the method is conducted on samples obtained on two or more occasions from the patient.

4. The method according to claim 1, wherein the samples are obtained prior to and/or during and/or following treatment for major depressive disorder.

5. The method according to claim 1, wherein the samples are taken at intervals over the remaining life, or a part thereof, of the patient.

6. The method according to claim 1, wherein quantifying is performed by measuring the concentration of ApoA-IV in each of the biological and reference samples.

7. The method according to claim 1, wherein detecting and/or quantifying is performed by one or more methods selected from the group consisting of SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC, other LC, and LC-MS-based technique.

8. The method according to claim 1, wherein detecting and/or quantifying is performed using an immunological method.

9. The method according to claim 1, wherein the detecting and/or quantifying is performed using a biosensor or a microanalytical, microengineered, microseparation or immunochromatography system.

10. The method according to claim 1, wherein the biological sample is cerebrospinal fluid, whole blood, blood serum, plasma, urine, saliva, or other bodily fluid, or breath, condensed breath, or an extract or purification therefrom, or dilution thereof.

11. A method according to claim 10, wherein the biological sample is whole blood, blood serum, or plasma.

12. A method of treating a patient suffering with depression, comprising:
   (a) obtaining a biological sample from the patient;
   (b) quantifying the amount of ApoA-IV in the biological sample;
   (c) comparing the amount of ApoA-IV in the biological sample with the amount present in one or more reference samples obtained from one or more responders to antidepressant treatment and/or one or more reference samples obtained from one or more non-responders to antidepressant treatment, and identifying the patient as a responder to antidepressant treatment if:
      (i) the level of ApoA-IV in the biological sample is equivalent to the level of ApoA-IV in the one or more reference sample from the one or more responders; or
      (ii) the level of ApoA-IV in the biological sample is lower than the level of ApoA-IV in the one or more reference sample from non-responders; and
   (d) administering an antidepressant to the patient identified as a responder patient to antidepressant treatment.

13. The method according to claim 1, wherein the patient is diagnosed with Major Depressive Disorder (MDD).

14. The method according to claim 13, wherein the patient is a recurrent Major Depressive Disorder patient or a first onset drug naïve Major Depressive Disorder patient.

15. The method according to claim 1, wherein the antidepressant is venlafaxine, imipramine, agomelatin, amitriptillin, cipralex, citalopram, doxepin, duloxetine, lithium, lorazepam, lormetazepam, mirtazapine, opipramol, paroxetine, reboxetin, remergil, risperidone, seroquel, sertraline, trancylcypromin, trimiparine, trimipramine, fluoxetine, escitalopram or a combination thereof.

16. The method according to claim 6, wherein the antidepressant is venlafaxine.

17. The method according to claim 12, wherein the patient is diagnosed with Major Depressive Disorder (MDD).

18. The method according to claim 16, wherein the patient is a recurrent Major Depressive Disorder patient or a first onset drug naïve Major Depressive Disorder patient.

19. The method according to claim 12, wherein the antidepressant is venlafaxine, imipramine, agomelatin, amitriptillin, cipralex, citalopram, doxepin, duloxetine, lithium, lorazepam, lormetazepam, mirtazapine, opipramol, paroxetine, reboxetin, remergil, risperidone, seroquel, sertraline, trancylcypromin, trimiparine, trimipramine, fluoxetine, escitalopram or a combination thereof.

20. The method according to claim 12, wherein the antidepressant is venlafaxine.

* * * * *